US009974656B2

(12) United States Patent
Pappas et al.

(10) Patent No.: US 9,974,656 B2
(45) Date of Patent: May 22, 2018

(54) FEMORAL NECK PROSTHESIS (75) Inventors: Christos Pappas, Agrinio (GR);
Robert John Andrew Bigsby,
Glamorgan (GB); **Gordon William
Blunn, Royston (GB); Poul T. Nielsen**,
Aalborg (GB)

(73) Assignee: Biomet UK Limited, Bridgend (GB)

( * ) Notice: Subject to any disclaimer, the term of this patent is extended or adjusted under 35 U.S.C. 154(b) by 462 days.

(21) Appl. No.: 13/392,001

(22) PCT Filed: Oct. 28, 2009

(86) PCT No.: PCT/GB2009/002565
§ 371 (c)(1),
(2), (4) Date: May 21, 2012

(87) PCT Pub. No.: WO2011/023921
PCT Pub. Date: Mar. 3, 2011

(65) Prior Publication Data
US 2012/0259422 A1  Oct. 11, 2012

(30) Foreign Application Priority Data

Aug. 27, 2009 (GB) .................................. 0914939.4

(51) Int. Cl.
*A61F 2/36* (2006.01)
*A61F 2/30* (2006.01)

(52) U.S. Cl.
CPC ... *A61F 2/3601* (2013.01); *A61F 2002/30116* (2013.01); *A61F 2002/30158* (2013.01); *A61F 2002/30332* (2013.01); *A61F 2002/30334* (2013.01); *A61F 2002/30359* (2013.01); *A61F 2002/30616* (2013.01); *A61F 2002/30729* (2013.01); *A61F 2002/365* (2013.01); *A61F 2002/3625* (2013.01); *A61F 2002/3631* (2013.01); *A61F 2002/3652* (2013.01); *A61F 2002/3678* (2013.01);
(Continued)

(58) Field of Classification Search
CPC .......................................................... A61F 2/36
USPC ...................................................... 623/23.22
See application file for complete search history.

(56) References Cited

U.S. PATENT DOCUMENTS

| 4,608,055 A | 8/1986 | Morrey |
| 7,854,767 B2 | 12/2010 | May et al. |
| 2004/0236430 A1* | 11/2004 | Koch ............... B22F 7/004 623/23.31 |

FOREIGN PATENT DOCUMENTS

| DE | 102004038281 B3 | 5/2006 |
| DE | 102006031573 A1 | 1/2008 |

(Continued)

OTHER PUBLICATIONS

International Search Report for PCT/GB2009/002565, ISA/EP, Rijswijk, NL, dated May 4, 2010.
(Continued)

*Primary Examiner* — Matthew Schall
(74) *Attorney, Agent, or Firm* — Schwegman Lundberg & Woessner, P.A.

(57) ABSTRACT

A femoral neck prosthesis (10) with a cross-section defined by a perimeter comprising: first and second arcuate portions (12, 14) disposed opposite one another; and first and second substantially straight portions (16, 18) disposed opposite one another and in between the first and second arcuate portions, wherein the first and second straight portions are non-parallel with respect to one another.

20 Claims, 9 Drawing Sheets (52) U.S. Cl.
CPC ............. *A61F 2220/0033* (2013.01); *A61F 2230/0006* (2013.01); *A61F 2230/0026* (2013.01)

(56) References Cited

FOREIGN PATENT DOCUMENTS

| EP | 2002804 A1 | 12/2008 |
|---|---|---|
| WO | WO-02100302 A1 | 12/2002 |

OTHER PUBLICATIONS

"European Application Serial No. 9756336.5, Examination Notification Art. 94(3) dated Oct. 5, 2015", 4 pgs.
"European Application Serial No. 9756336.5, Examination Notification Art. 94(3) dated Nov. 28, 2014", 4 pgs.
"European Application Serial No. 9756336.5, Office Action dated Apr. 5, 2012", 2 pgs.
"European Application Serial No. 9756336.5, Response filed Jan. 30, 2015 to Examination Notification Art. 94(3) dated Nov. 28, 2014", 13 pgs.
"European Application Serial No. 9756336.5, Response filed Jul. 6, 2012 to Office Action dated Apr. 5, 2012", 16 pgs.
"International Application Serial No. PCT/GB2009/002565, International Preliminary Report on Patentability dated Mar. 8, 2012", 7 pgs.
"International Application Serial No. PCT/GB2009/002565, Written Opinion dated May 4, 2010", 5 pgs.

\* cited by examiner

FEMORAL NECK PROSTHESIS

CROSS-REFERENCE TO RELATED APPLICATIONS

This application is a 371 U.S. National Stage of International Application No. PCT/GB2009/002565, filed Oct. 28, 2009, which claims the benefit of United Kingdom Patent Application No. GB 0914939.4, filed Aug. 27, 2009. The disclosures of the above applications are incorporated herein by reference.

This invention relates to a femoral neck prosthesis and particularly but not exclusively relates to a femoral neck prosthesis with a trapezoidal cross-section.

BACKGROUND

Arthritis of the hip primarily affects the articulation between the femoral head and the acetabulum. If surgery is required, the primary objective is to replace the articulating surfaces. To achieve this it is desirable to obtain a homogeneous transfer of forces to the proximal femur. This is best provided by retention of the femoral neck. Early attempts to achieve a conservation of the femoral neck and more physiological loading were betrayed by poor materials, inadequate fixation and failure of the articulation. Despite the high level of survivorship of cemented and uncemented stemmed femoral components, there is a need for a joint prosthesis that does not invade the femoral canal. The above mentioned prosthesis would be useful in treating younger and more active patients, in whom the use or such a design would usefully prolong the time where a conventional total joint replacement design is necessary.

While the more frequent use of hard-hard articulations and the highly cross-linked polyethylenes in total hip replacement are anticipated to lead to a reduction of osteolysis, in addition to wear, stress shielding is expected to become a more targeted cause of bone reduction. The reduction of stress and strain in the proximal femur following total hip replacement is hypothesized to be one reason of proximal bone loss, which may lead to a reduction of implant support, progressive implant subsidence and periprosthetic bone fracture. Even though it is not clear if the resorption of the proximal femoral bone stock is directly related to the survival of implants, an excessive bone loss around a primary prosthesis can reduce the longevity of a revision prosthesis by compromising the bone stock available at the revision procedure. Thus, conservation of bone stock is a vitally important principle, especially in young patients where the chances of revisions during the patients' lifetime are high. Particularly in uncemented total hip replacement, which is often favored in young patients, the stem geometry is believed to play an important role in the load transfer to the femur and, consequently, in femoral remodeling. As canine studies, periprosthetic bone mineral density measurements and clinical observations have indicated, implantation of different femoral stems lead to a bone reaction specific for the geometry, surface finish and stiffness of the implants used.

The main problem with the replacement procedure is the survival rate and the revision options. At a revision there is a considerable amount of bone of the upper femur destroyed in the loosening process, and during the removal procedure of the existing femoral component. The subsequent revision implant is necessarily larger and longer in order to gain sufficient fixation. The survivorship of such devices is usually less than that of the primary procedure. Moreover, should that device fail, the prognosis is very poor indeed. Hence, there is a strong rationale for use of a "conservative" device at the primary stage, which involves interfacing with far less of the femur than does a conventional total hip. The goals of such a conservative device are that it will be easy to insert and will have a survivorship similar to that of a conventional total hip. Even if the survivorship was slightly less, there is still a justification for its use. If a conservative hip is suitably designed and if it were to fail by loosening or other reason, then its removal would involve little destruction of the femoral bone. The revision procedure would then be equivalent to the use of a primary total hip. Thereby, the patient would have gained a substantial time period, say ten years or more. The high probability of revision in these younger more active patients has been one of the main factors driving the quest for more bone sparing conservative options at a total hip replacement. The present invention therefore seeks to address this issue.

STATEMENTS OF INVENTION

According to a first aspect of the present invention there is provided a femoral neck prosthesis with a cross-section defined by a perimeter comprising: first and second arcuate portions disposed opposite one another; and first and second substantially straight portions disposed opposite one another and in between the first and second arcuate portions, wherein the first and second straight portions are non-parallel with respect to one another.

The first and second arcuate portions may have the same radius of curvature. The first and second arcuate portions may have the same centre of curvature.

The perimeter may be symmetrical about a line of symmetry intersecting the first and second arcuate portions. The distance between first and second straight portions along a line perpendicular to the line of symmetry and passing through a midpoint in the line of symmetry may be substantially two-thirds of the distance between the first and second arcuate portions along the line of symmetry.

The first and second arcuate portions may be provided on medial and lateral sides of the patient respectively. The first and second substantially straight portions may be provided on anterior and posterior sides of the patient respectively. The first and second substantially straight portions may converge such that the distance between the first and second substantially straight portions may be greater at the lateral side than the medial side.

The cross-sectional area of the femoral neck prosthesis may vary along the length of the prosthesis. The cross-sectional area of the femoral neck prosthesis may taper along the length of the prosthesis. A locus defined by a midpoint between the first and second arcuate portions along the length of the femoral neck prosthesis may be substantially straight.

A substantial portion of the femoral neck prosthesis may be suitable for placement within the metaphyseal cancellous bone between the femoral head and the cortical bone.

The corners between the first and second arcuate portions and the first and second substantially straight portions may be rounded off.

A femoral neck prosthesis assembly may comprise the femoral neck prosthesis as described above. The femoral neck prosthesis assembly may further comprise a neck portion for engaging a femoral head portion. The neck portion may be modular and may have first and second ends adapted to selectively engage corresponding openings in the prosthetic femoral neck and the femoral head portion respectively. The prosthetic assembly may further comprise a modular collar. The modular collar may have an opening to selectively engage the neck portion of the prosthetic assembly.

According to a second aspect of the invention there is provided a method of manufacturing the femoral neck prosthesis as described above, wherein the method comprises: providing a workpiece having a cross-section with an at least partially curved perimeter; and removing first and second portions from the workpiece such that first and second segments are removed from the cross-section of the workpiece. The cross-section of the workpiece may be circular.

A femoral neck prosthesis according to an example of the present invention may be based on the principle of transmitting physiological load through the trabeculae between the femoral head and different endosteal regions of the proximal femur as naturally as possible. The prosthesis may provide rigid fixation that would withstand all the forces and moments transmitted from the femoral head. The prosthesis may further leave the femur sufficiently intact if the prosthesis had to be removed. In that case, a conventional hip replacement stem may be inserted with minimal compromise. Based on the anatomical shape of the neck of the femur, a trapezoidal cross section may provide optimum fit and fill allowing for loading on to the calcar region. A tapered section along the length of the prosthesis may produce compressive and shear forces down the axis of the femoral neck. The forces may be transmitted from the shaft of the prosthesis to the cortical and cancellous bone in the region of the femoral neck. The femoral neck may then further distribute the loading in the distal part of the femur.

BRIEF DESCRIPTION OF THE DRAWINGS

For a better understanding of the present invention, and to show more clearly how it may be carried into effect, reference will now be made, by way of example, to the accompanying drawings, in which:—

FIG. 1 shows a femoral neck prosthesis according to an example of the present invention in a perspective view (FIG. 1(a)) and a plan view (FIG. 1(b));

DETAILED DESCRIPTION

With reference to FIG. 2 a femoral neck prosthesis 10 according to an example of the present invention comprises a cross-section defined by a perimeter comprising first and second arcuate portions 12, 14 and first and second substantially straight portions 16, 18. Accordingly, the perimeter has four sides. The first and second arcuate portions 12, 14 are disposed opposite one another. The first and second substantially straight portions 16, 18 are disposed opposite one another and in between the first and second arcuate portions 12, 14. The first and second straight portions 16, 18 converge. In other words they are not parallel.

Figure 2A:
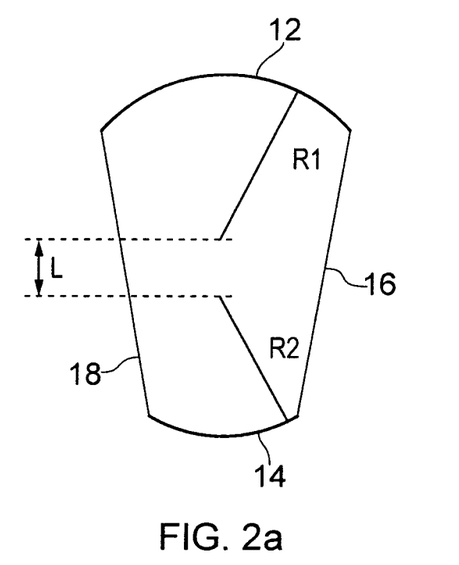
FIGS. 2(a)-(d) shows a sectional view of the femoral neck prosthesis according to an example of the present invention.
Figure 2B:
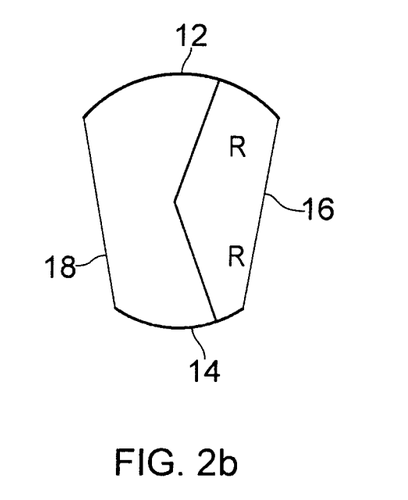

As shown in FIG. 2(a), the first and second arcuate portions 12, 14 may have different radii of curvature and/or different centres of curvature. For example, the first and second arcuate portions may have radii R1 and R2 respectively and their centres of curvature may be separated by a distance L. Furthermore, the first and second arcuate portions 12, 14 need not be circular in shape and may be elliptical or any other curved shape. However, with reference to FIG. 2(b), the first and second arcuate portions 12, 14 may have the same radius and centre of curvature. In other words, the first and second arcuate portions 12, 14 may be arcs from the same circle.

Figure 1A:
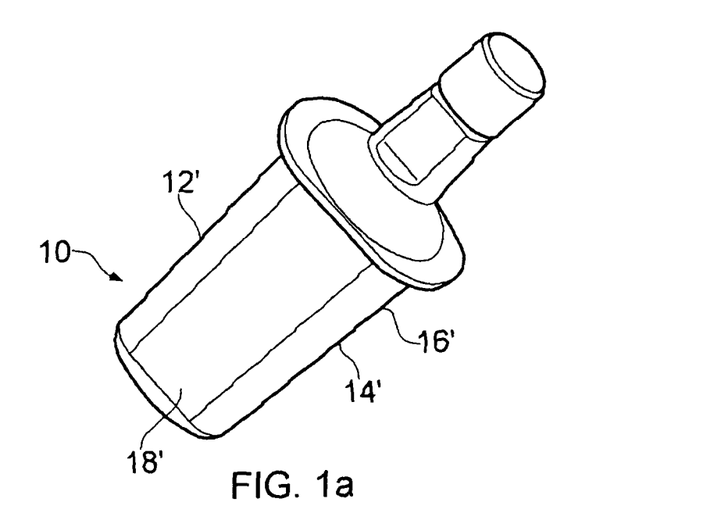

Referring to FIGS. 1(a) and 2(a), the cross-section described above extends in a lengthwise direction so as to generate first and second arcuate surfaces 12', 14' and first and second substantially straight surfaces 16', 18'. The first and second substantially straight surfaces 16', 18' may be straight in the plane of the above described cross-section, but may be curved or straight in a lengthwise direction. Similarly, the first and second arcuate surfaces 12', 14' may be curved in the plane of the above described cross-section, but may be curved or straight in a lengthwise direction. The first and second substantially straight surfaces 16', 18' resist rotation of the femoral neck 10 when in situ, whilst also maximising the amount of bone remaining.

The first and second arcuate surfaces 12', 14' are provided on lateral and medial sides of the patient respectively and the first and second substantially straight surfaces 16', 18' are provided on posterior and anterior sides of the patient respectively. The first and second substantially straight portions 16, 18 converge such the distance between the first and second substantially straight portions is greater at the lateral side than the medial side.

The cross-sectional area of the femoral neck prosthesis 10 may vary along the length of the prosthesis and the femoral neck prosthesis may taper towards its distal end. Alternatively, the cross-sectional area may be constant along the length of the femoral neck prosthesis. A locus defined by a midpoint between the first and second arcuate portions 12, 14 along the length of the prosthesis is substantially straight. In the particular case of the first and second arcuate portions 12, 14 having the same radii and centres of curvature, the midpoint corresponds to the centre of curvature.

Figure 2C:
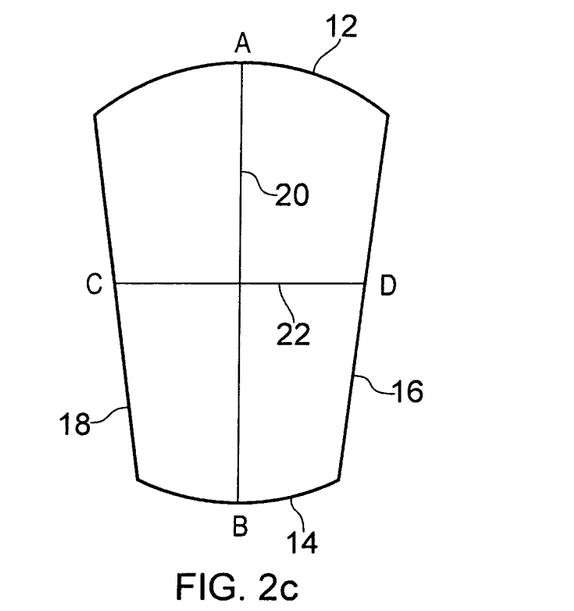

With reference to FIG. 2(c), the cross section of the perimeter of the prosthesis is symmetrical about a line of symmetry 20 intersecting the first and second arcuate portions 12, 14. In the particular case of the first and second arcuate portions being defined by a common circle, the line of symmetry corresponds to a diameter of the circle. The distance between the first and second straight portions 16, 18 along a line 22 perpendicular to the line of symmetry and passing through a midpoint in the line of symmetry 20 is substantially two-thirds of the distance between the first and second arcuate portions along the line of symmetry. In other words, the ratio of the lengths of the lines CD:AB shown in FIG. 2 is 2:3.

Figure 2D:
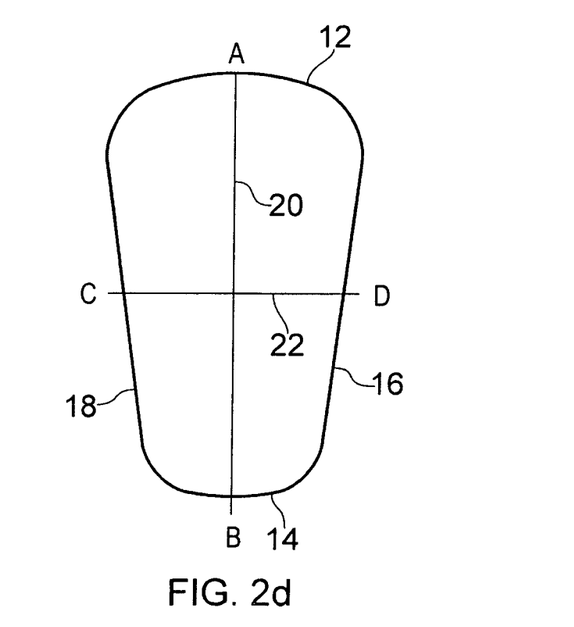

As shown in FIG. 2(d), the corners between the first and second arcuate portions 12, 14 and the first and second substantially straight portions 16, 18 may be optionally rounded off.

Figure 3A:
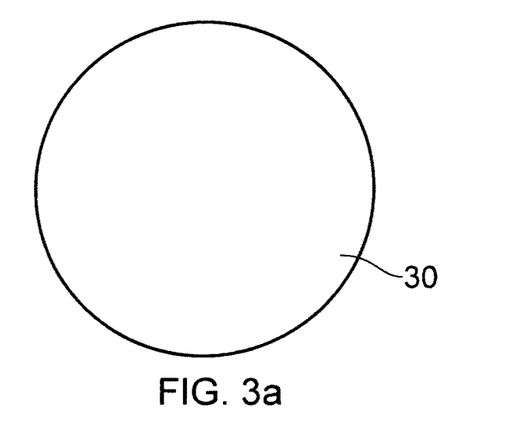
FIGS. 3(a)-(d) show a sectional view of the femoral neck prosthesis according to an example of the present invention at various stages during manufacture.

With reference to FIGS. 3(a)-(d) the femorla neck prosthesis 10 described above may be manufactured by providing a workpiece 30 having an at least partially curved cross-section, which may in one particular example be a circular cross-section as shown in FIG. 3(a). The workpiece may for example be tubular, frustoconical or cylindrical.

Figure 3B:
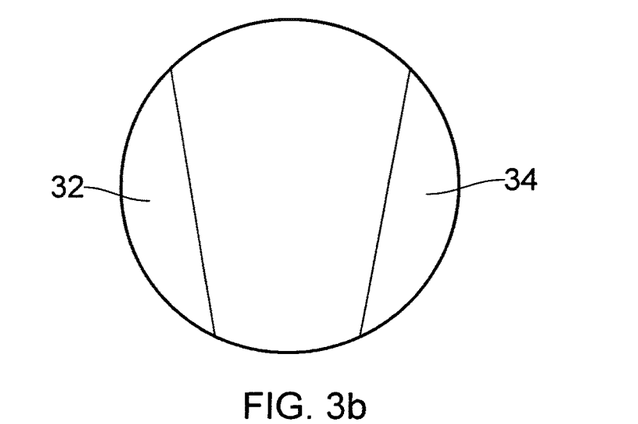
Figure 3C:
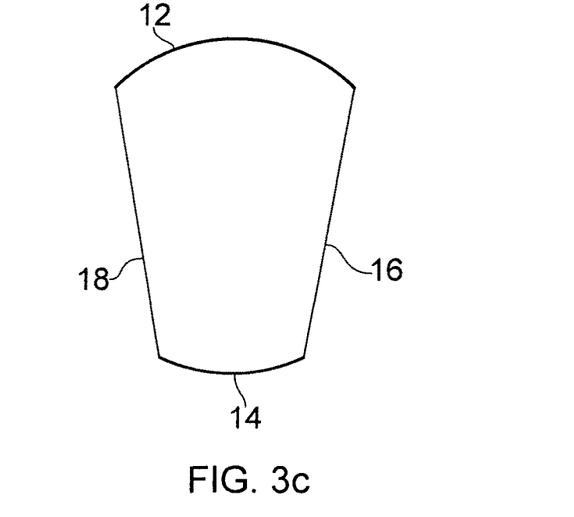
Figure 3D:
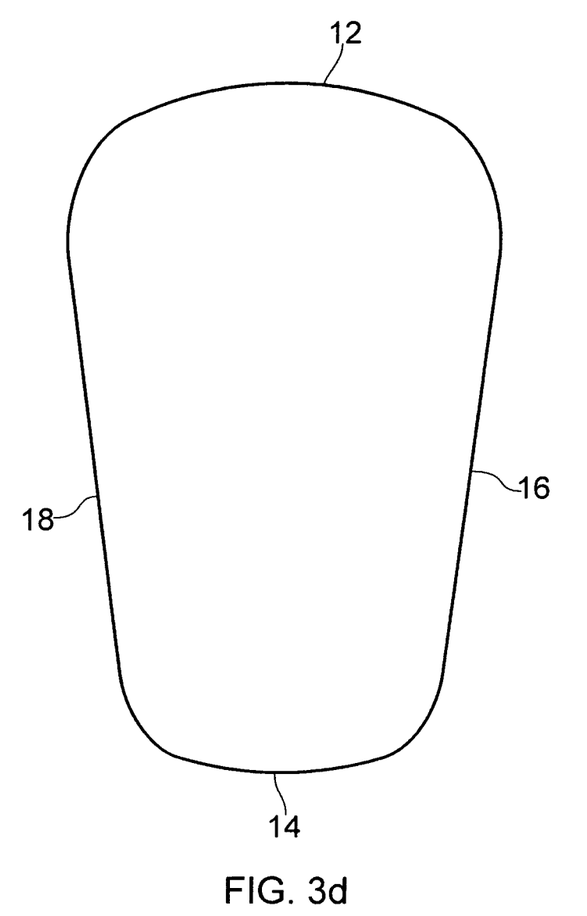

First and second portions 32, 34 are then removed from the workpiece 30 by cutting, milling, grinding or any other removal process (FIG. 3(b)). The first and second portions 32, 34 have a cross-section such that first and second segments are effectively removed from the cross-section of the workpiece. The net result is that the first and second substantially straight portions 16, 18 are formed (FIG. 3(c)). Alternatively, the femoral neck prosthesis may be formed in a mould. However, the mould may be formed in a manner similar to that described above, i.e. from an at least partially curved cross-section workpiece with segments removed. In either case, manufacturing the femoral neck prosthesis 10 is straightforward as the cross-section of the workpiece may form two of the four sides of the perimeter and the remaining two straight edged sides are readily formed. The corners may subsequently be rounded off as shown in FIG. 4(d). (FIG. 3(d) contrasts with FIGS. 3(a)-(c) in that it shows a workpiece cross-section comprising first and second arcuate portions with different centres and radii of curvature.)

Figure 4A:
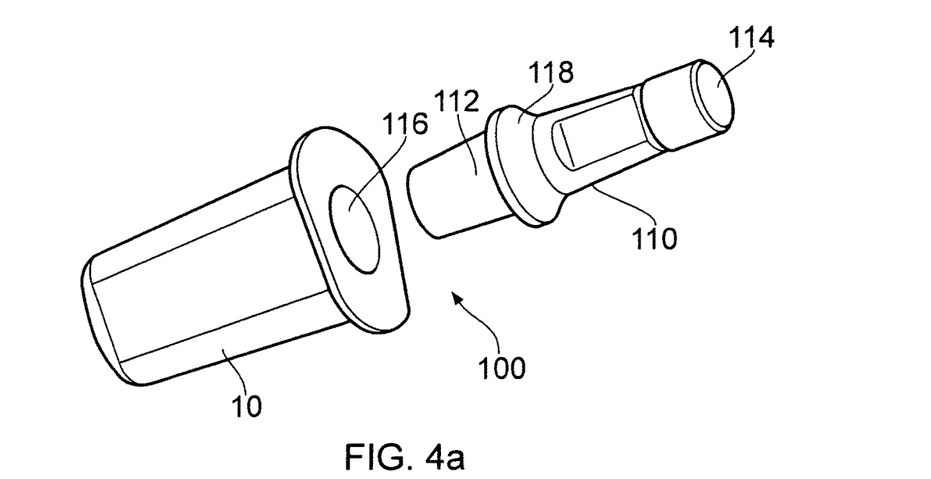
FIGS. 4(a)-(c) show a femoral neck prosthesis assembly comprising a neck portion according to an example of the present invention.
Figure 4B:
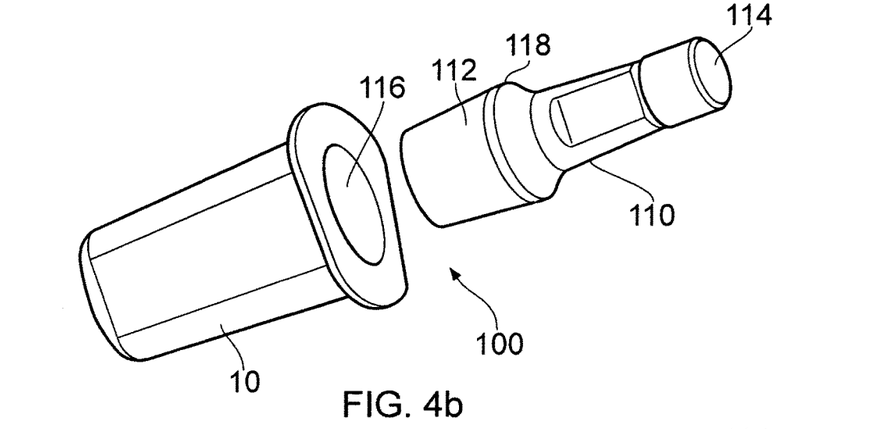
Figure 4C:
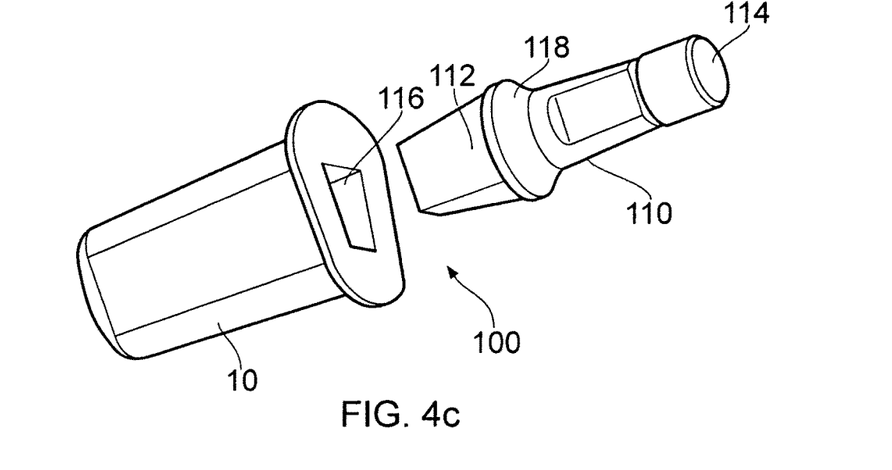

With reference to FIGS. 4(a)-(c) a femoral neck prosthesis assembly 100 according to an example of the present invention comprises the femoral neck prosthesis 10 as described above and a neck portion 110 for engaging a femoral head portion (not shown). The neck portion 110 is removable from the femoral neck prosthesis 10 and femoral head. In other words the neck portion 110 is modular. The neck portion 110 has first and second ends 112, 114 adapted to selectively engage corresponding openings in the femoral neck prosthesis and the femoral head portion respectively. For example, the femoral neck prosthesis 10 comprises an opening 116 for receiving the first end 112 of the neck portion 110. The opening 116 and first end 112 of the neck portion 110 may be correspondingly tapered in order to provide a tapered fit. The first end 112 of the neck portion 110 and the corresponding opening 116 may comprise a circular cross-section (FIG. 5(a)), an elliptical cross-section (FIG. 5(b)), a trapezoidal cross-section (FIG. 5(c)) or any other suitable cross-section. The second end 114 of the neck portion 110 may comprise a similarly tapered connection.

The neck portion 110 may further comprise an abutment shoulder 118 at the first end 112 of the neck portion which may abut against the femoral neck prosthesis 10.

Figure 1B:
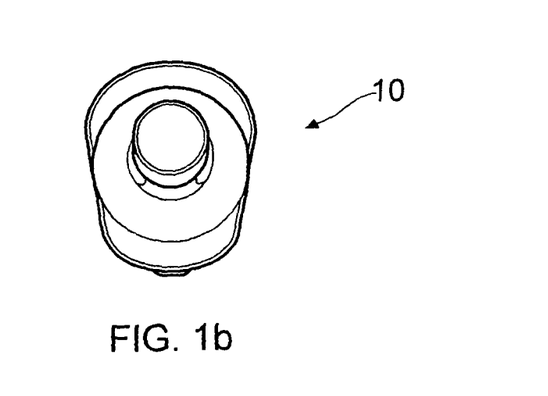
Figure 5A:
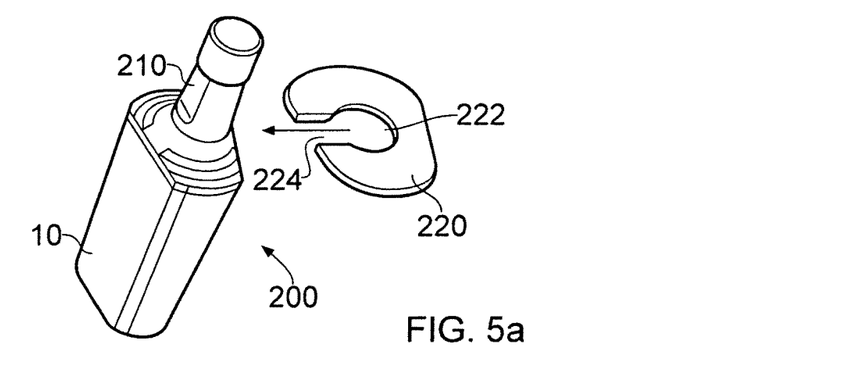
FIGS. 5(a)-(c) show a femoral neck prosthesis assembly comprising a collar according to an example of the present invention.
Figure 5B:
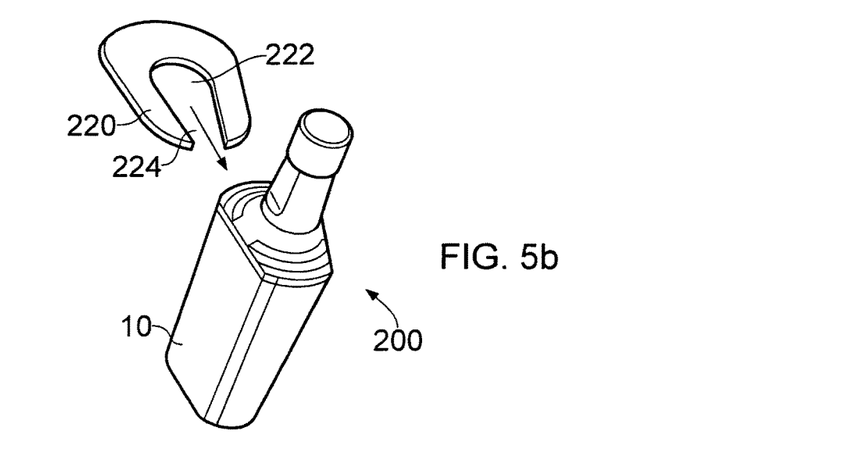
Figure 5C:
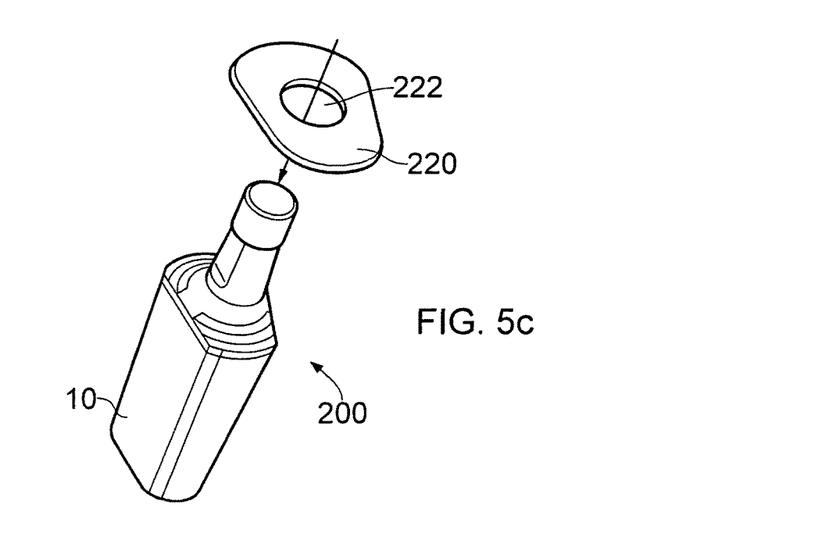

With reference to FIGS. 5(a)-(c) a femoral neck prosthesis assembly 200 according to an example of the present invention comprises the femoral neck prosthesis 10 as described above and a collar 220 for engaging a resected portion of the femur. The collar 220 is disposed about a neck portion 210 of the femoral neck prosthesis 10 which may or may not be removable. The collar 220 is removable from the femoral neck prosthesis 10. In other words the collar 220 is modular. The collar 220 comprises an opening 222 shaped to selectively engage the neck portion 210 of the prosthetic assembly. The collar may comprise an additional opening 224 such that the opening 222 is only partially enclosed by the collar. The collar may then be installed onto the neck portion 210 from a anterior or posterior side (as shown in FIG. 5(a)) or a medial or lateral side (as shown in FIG. 5(b)). The additional opening 224 may be tapered such that the collar 22 snaps into position about the neck portion 210. Alternatively, the collar 220 may not comprise the additional opening 224 such that the opening 222 is enclosed by the collar (FIG. 5(c)). The collar may then be installed from the femoral head end of the neck portion 210. As shown in FIG. 1(b), the collar 220 may have a cross-section similar to the cross-section of the femoral neck prosthesis 10. The collar 220 may have a larger cross-sectional area that the femoral neck prosthesis 10 so as to protrude beyond the femoral neck prosthesis 10 and provide an abutment surface for abutment with the femoral neck.

Figure 6:
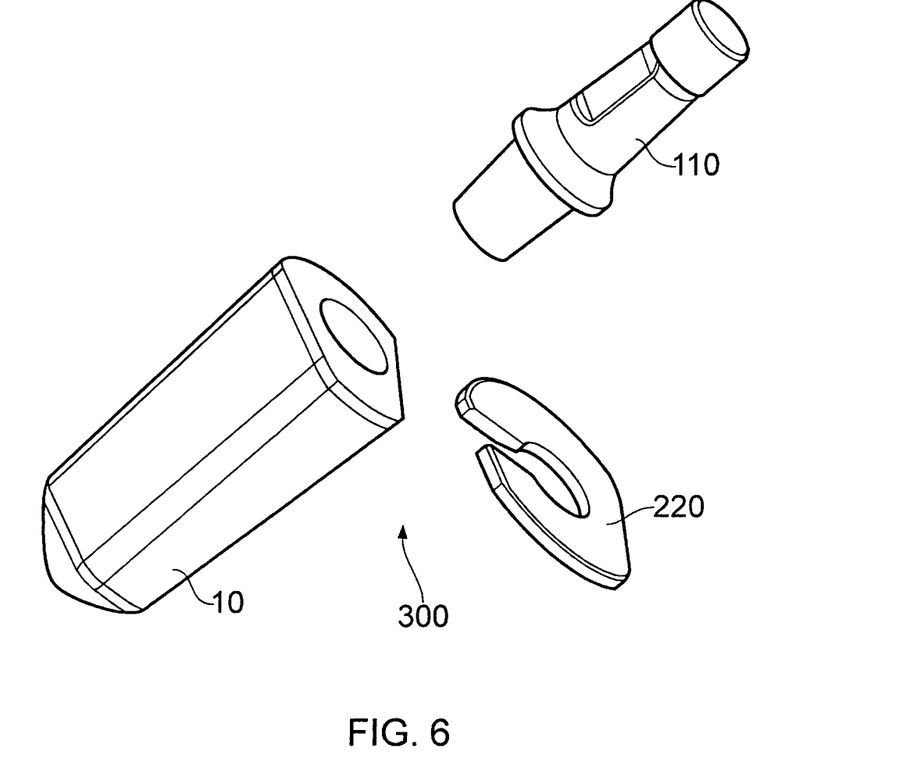
FIG. 6 shows a femoral neck prosthesis assembly comprising a neck portion and a collar according to an example of the present invention.

With reference to FIG. 6 a femoral neck prosthesis assembly 300 according to an example of the present invention comprises the femoral neck prosthesis 10 as described above, a removable collar 220 for engaging a resected portion of the femur and a removable neck portion 110 for engaging a femoral head portion (not shown). In other words, the prosthetic femoral assembly 300 may comprise both the modular collar 220 and the modular neck portion 110 described above. Advantageously, modular collars and/or modular neck portions allow different sized or shaped collars or neck portions to be used to suit the requirements of the patient. It also permits a greater variation in the femoral assembly with the minimum number of parts required.

Figure 7:
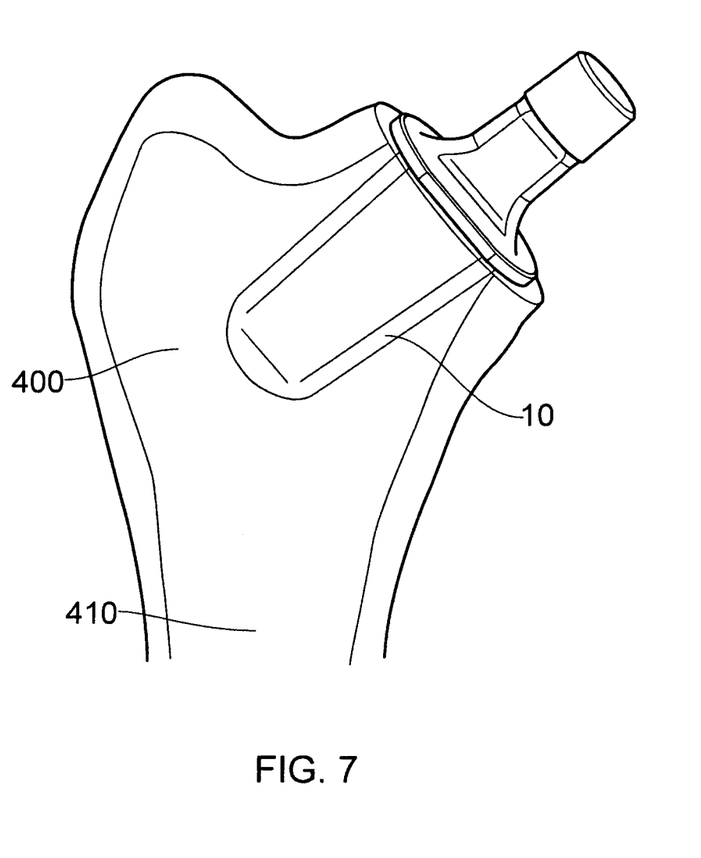
FIG. 7 shows a perspective view of the femoral neck prosthesis according to an example of the present invention once installed in the femur.

With reference to FIG. 7 a perspective view of the femoral neck prosthesis 10 once installed in the femur is shown. As is shown, a substantial portion of the femoral neck prosthesis is suitable for placement within the metaphyseal cancellous bone 400 between the femoral head and the proximal cortical bone 410. The amount of bone remaining is therefore maximised, thereby facilitating revision surgery.

Anatomical forces are transmitted through the trabeculae between the femoral head and different endosteal regions of the upper femur. A rigid fixation which withstands all the forces and moments transmitted from the femoral head is therefore provided. The resultant force on the femoral head produces a compressive force down the axis of the neck portion and a perpendicular shear force. The compressive force is transmitted by the collar of the implant to the cut surface of the femoral neck. The shear force will be transmitted by the femoral neck prosthesis from adjacent the collar to the cortical and cancellous bone in that region of the medial neck. Furthermore, the femur is left sufficiently intact so that, if the prosthesis had to be removed, a conventional hip replacement stem could be inserted with minimal compromise.

The invention claimed is:

1. A femoral neck prosthesis with a cross-section defined by a perimeter comprising:
    first and second arcuate portions disposed opposite one another, each having a first end and a second end; and
    first and second substantially straight portions disposed opposite one another and each having a first end and a second end, wherein the first end of the first arcuate portion is connected to the first end of the first straight portion, the second end of the first arcuate portion is connected to the first end of the second straight portion, the first end of the second arcuate portion is connected to the second end of the first straight portion, and the second end of the second arcuate portion is connected to the second end of the second straight portion, and wherein the first and second straight portions are non-parallel with respect to one another,
    wherein a locus, defined by a midpoint between the first and second arcuate portions along a length of the femoral neck prosthesis, is substantially straight,
    wherein a distal end of the femoral neck prosthesis is configured for placement within a metaphyseal cancellous bone of a femur between a femoral head and a cortical bone such that when the prosthesis is in an installed configuration the distal end is positioned in the metaphyseal cancellous bone, and wherein the femoral neck prosthesis is configured such that in an installed configuration a rigid fixation between the femoral neck prosthesis and the femur is provided, the rigid fixation withstanding all physiological forces and moments transmitted from the femoral head, with the physiological forces being transmitted through a trabeculae between the femoral head and different endosteal regions of the upper femur.

2. The femoral neck prosthesis as claimed in claim 1, wherein the first and second arcuate portions have an equal radius of curvature.

3. The femoral neck prosthesis as claimed in claim 1, wherein the first and second arcuate portions have an equal center of curvature.

4. The femoral neck prosthesis as claimed in claim 1, wherein the perimeter is symmetrical about a line of symmetry intersecting the first and second arcuate portions.

5. The femoral neck prosthesis as claimed in claim 4, wherein a distance between the first and second straight portions along a line perpendicular to the line of symmetry and passing through a midpoint in the line of symmetry is substantially two-thirds of the distance between the first and second arcuate portions along the line of symmetry.

6. The femoral neck prosthesis as claimed in claim 1, wherein the first and second arcuate portions are provided on lateral and medial sides of a patient respectively and the first and second substantially straight portions are provided on posterior and anterior sides of the patient respectively.

7. The femoral neck prosthesis as claimed in claim 6, wherein the first and second substantially straight portions converge such that a distance between the first and second substantially straight portions is greater at the lateral side than the medial side.

8. The femoral neck prosthesis as claimed in claim 1, wherein the cross-sectional area of the femoral neck prosthesis varies along a length of the femoral neck prosthesis.

9. The femoral neck prosthesis as claimed in claim 1, wherein corners between the first and second arcuate portions and the first and second substantially straight portions are rounded off.

10. A femoral neck prosthesis assembly comprising the femoral neck prosthesis as claimed in claim 1, wherein the femoral neck prosthesis assembly further comprises a neck portion for engaging a femoral head portion.

11. The femoral neck prosthesis assembly as claimed in claim 10, wherein the neck portion is modular and has first and second ends adapted to selectively engage corresponding openings in the femoral neck prosthesis and the femoral head portion respectively.

12. The femoral neck prosthesis assembly as claimed in claim 10, wherein the femoral neck prosthesis assembly further comprises a modular collar, the modular collar having an opening to selectively engage the neck portion of the femoral neck prosthesis assembly.

13. A femoral neck prosthesis having a distal end and a proximal end, the femoral neck prosthesis comprising:
a cross-section defined by a perimeter comprising:
first and second arcuate portions disposed opposite one another; and
first and second substantially straight portions disposed opposite one another, the first and second substantially straight portions disposed in between and connected to the first and second arcuate portions; and
a locus defined by a midpoint between the first and second arcuate portions along a length of the femoral neck prosthesis from the distal end to the proximal end, the locus being substantially straight,
wherein the distal end of the femoral neck prosthesis is configured for placement within a metaphyseal cancellous bone of a femur between a femoral head and a cortical bone such that, when the prosthesis is in an installed configuration, the distal end is positioned in the metaphyseal cancellous bone.

14. The femoral neck prosthesis as claimed in claim 13, wherein the first and second straight portions are non-parallel with respect to one another.

15. The femoral neck prosthesis as claimed in claim 13, wherein the first and second arcuate portions have an equal radius of curvature.

16. The femoral neck prosthesis as claimed in claim 13, wherein the first and second arcuate portions are configured for implantation on lateral and medial sides of a patient respectively and the first and second substantially straight portions are configured for implantation on posterior and anterior sides of the patient respectively.

17. The femoral neck prosthesis as claimed in claim 16, wherein the first and second substantially straight portions converge such that a distance between the first and second substantially straight portions is greater at the lateral side than the medial side.

18. The femoral neck prosthesis as claimed in claim 13, wherein the cross-sectional area of the femoral neck prosthesis varies along the length of the femoral neck prosthesis.

19. A femoral neck prosthesis assembly comprising the femoral neck prosthesis as claimed in claim 13, wherein the femoral neck prosthesis assembly further comprises a neck portion for engaging a femoral head portion.

20. The femoral neck prosthesis assembly as claimed in claim 19, wherein the neck portion is modular and has first and second ends adapted to selectively engage corresponding openings in the femoral neck prosthesis and the femoral head portion respectively.

* * * * *